US008657798B2

(12) United States Patent
Shibata et al.

(10) Patent No.: US 8,657,798 B2
(45) Date of Patent: Feb. 25, 2014

(54) ANTI-INFLAMMATORY ANALGESIC ADHESIVE PATCH FOR EXTERNAL USE

(75) Inventors: Taiki Shibata, Higashikagawa (JP); Yuichiro Mabuchi, Higashikagawa (JP); Kenichi Hattori, Higashikagawa (JP); Takashi Kamakura, Higashikagawa (JP)

(73) Assignees: Teikoku Seiyaku Co., Ltd., Kagawa (JP); IBSA Institut Biochimique SA, Massagno (CH)

( * ) Notice: Subject to any disclaimer, the term of this patent is extended or adjusted under 35 U.S.C. 154(b) by 0 days.

(21) Appl. No.: 13/520,431

(22) PCT Filed: Jan. 5, 2011

(86) PCT No.: PCT/JP2011/050021
§ 371 (c)(1),
(2), (4) Date: Jul. 6, 2012

(87) PCT Pub. No.: WO2011/083787
PCT Pub. Date: Jul. 14, 2011

(65) Prior Publication Data
US 2012/0283671 A1 Nov. 8, 2012

(30) Foreign Application Priority Data
Jan. 7, 2010 (JP) ................................. 2010-002188

(51) Int. Cl.
*A61F 13/02* (2006.01)
*A61F 15/00* (2006.01)
*A61F 13/00* (2006.01)

(52) U.S. Cl.
USPC ............................. 604/307; 424/443; 602/58

(58) Field of Classification Search
USPC ............................. 604/307; 424/443; 602/58
See application file for complete search history.

(56) References Cited

U.S. PATENT DOCUMENTS

| 4,738,848 | A | 4/1988 | Yoshida et al. |
| 4,948,805 | A | 8/1990 | Ziggiotti et al. |

(Continued)

FOREIGN PATENT DOCUMENTS

| CN | 1489996 | 4/2004 |
| CN | 101530401 | 9/2009 |

(Continued)

OTHER PUBLICATIONS

International Search Report issued Mar. 1, 2011 in International (PCT) Application No. PCT/JP2011/050021, of which the present application is the national stage.

(Continued)

*Primary Examiner* — Jacqueline Stephens
*Assistant Examiner* — Andrew J Mensh
(74) *Attorney, Agent, or Firm* — Wenderoth, Lind & Ponack, L.L.P.

(57) ABSTRACT

An external patch containing diclofenac hydroxyethylpyrrolidine prepared by laminating an adhesive layer on a backing, wherein said adhesive layer is characterized by comprising 5-50% by weight of styrene•isoprene•styrene block copolymer, 20-50% by weight of a tackifier resin, 5-70% by weight of a softening agent, and 0.5-20% by weight of one or more solubilizers selected from N-methyl-2-pyrrolidone, propylene glycol and dimethyl sulfoxide as essential ingredients, and 0.5-20% by weight of diclofenac hydroxyethylpyrrolidine as an active ingredient. The patch has excellent transdermal absorption, less skin-irritation and excellent stability of the drug.

2 Claims, 1 Drawing Sheet

(56) References Cited

U.S. PATENT DOCUMENTS

| | | | |
|---|---|---|---|
| 5,607,690 | A | 3/1997 | Akazawa |
| 6,914,169 | B1 * | 7/2005 | Oota et al. .................. 602/58 |
| 2003/0077297 | A1 | 4/2003 | Chen et al. |
| 2003/0175331 | A1 * | 9/2003 | Sasaki et al. .................. 424/449 |
| 2004/0037872 | A1 | 2/2004 | Liebschutz et al. |
| 2008/0089926 | A1 | 4/2008 | Ishima et al. |
| 2009/0022778 | A1 | 1/2009 | Yamaji et al. |
| 2010/0239639 | A1 * | 9/2010 | Suzuki et al. .................. 424/443 |
| 2011/0160194 | A1 | 6/2011 | Inoo et al. |

FOREIGN PATENT DOCUMENTS

| | | |
|---|---|---|
| EP | 372527 A1 * | 6/1990 |
| JP | 4-178323 | 6/1992 |
| JP | 6-305958 | 11/1994 |
| JP | 63-152372 | 6/1998 |
| JP | 2004-508397 | 3/2004 |
| JP | 2008-143866 | 6/2008 |
| JP | 2008-522957 | 7/2008 |
| WO | 2006/092829 | 9/2006 |
| WO | 2009/154148 | 12/2009 |

OTHER PUBLICATIONS

English translation of International Preliminary Report on Patentability and Written Opinion issued Aug. 7, 2012 in International (PCT) Application No. PCT/JP2011/050021, of which the present application is the national stage.

Machine translation of JP 2008-143866, Jun. 26, 2008.

Extended European Search Report issued Jun. 27, 2013 in corresponding European patent application No. 11 73 1785.

Bradley S. Galer, MD, Michael Rowbotham, MD, Jill Perander, Allison Devers, and Erika Friedman, "*Topical Diclofenac Patch Relieves Minor Sports Injury Pain: Results of a Multicenter Controlled Clinical Trial*", Journal of Pain and Symptom Management, vol. 19, No. 4, Apr. 4, 2000, pp. 287-294.

* cited by examiner

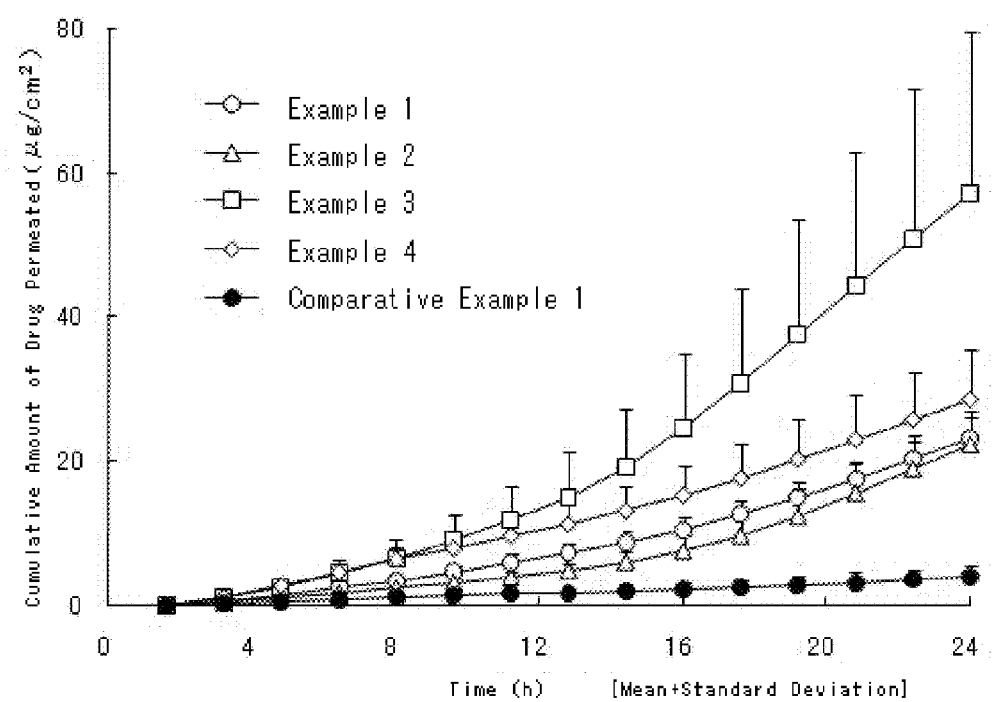

ANTI-INFLAMMATORY ANALGESIC ADHESIVE PATCH FOR EXTERNAL USE

TECHNICAL FIELD

The present invention relates to an oily patch containing diclofenac hydroxyethylpyrrolidine which has excellent transdermal absorption and stability of said drug as well as low irritation to the skin.

BACKGROUND ART

Diclofenac hydroxyethylpyrrolidine which is one of diclofenac salts has lower melting point than diclofenac sodium and is a medicament suitable for a transdermal absorption preparation (Patent document 1). Also, as diclofenac hydroxyethylpyrrolidine has better water solubility than diclofenac sodium and excellent compatibility with an aqueous base material, a cataplasm containing diclofenac hydroxyethylpyrrolidine has been developed until now (Patent document 2). However, in general, the cataplasm has problems such as insufficient transdermal absorption of the drug, and low adhesiveness to the skin.

Patent document 1: Japanese Patent Publication A 63-152372
Patent document 2: Japanese Patent Publication A 6-305958

DISCLOSURE OF INVENTION

Problems to be Solved by the Invention

The objects of the present invention are to solve the above-mentioned problems and to provide an external patch containing diclofenac hydroxyethylpyrrolidine which has excellent transdermal absorption of the drug and low irritation to the skin as well as excellent stability of the drug.

Means for Solving the Problems

As a consequence of the present inventors' extensive study to solve the above-mentioned problems, they have proved that the problems were solved by combining the drug and specific solubilizers to form an oily patch and finally completed the present invention.

More specifically, the present invention is related to an oily external patch containing diclofenac hydroxyethylpyrrolidine prepared by laminating an adhesive layer on a backing, wherein said adhesive layer is characterized by comprising 5-50% by weight of styrene•isoprene•styrene block copolymer, 20-50% by weight of a tackifier resin, 5-70% by weight of a softening agent, and 0.5-20% by weight of one or more solubilizers selected from N-methyl-2-pyrrolidone, propylene glycol and dimethyl sulfoxide as essential ingredients, and 0.5-20% by weight of diclofenac hydroxyethylpyrrolidine as an active ingredient.

Effect of the Invention

As the external patch of the present invention comprises the above-mentioned composition, the present invention has the effects such as providing a patch which has excellent transdermal absorption of diclofenac hydroxyethylpyrrolidine and low irritation to the skin as well as excellent preservation stability.

BRIEF DESCRIPTION OF DRAWINGS

FIG. 1 is a graph showing the result of rat skin permeability test in vitro on Test Example 1.

BEST MODE FOR CARRYING OUT THE INVENTION

The amount of diclofenac hydroxyethylpyrrolidine of the present invention is 0.5-20% by weight, preferably 1-10% by weight. When the amount of diclofenac hydroxyethylpyrrolidine is 0.5% by weight or less, the pharmacological efficacy is insufficient, and when the amount is 20% by weight or more, it has adverse effects on physical properties of the preparation such as crystallization of the drug in the preparation.

As the solubilizers of diclofenac hydroxyethylpyrrolidine of the present invention, one or more agents selected from N-methyl-2-pyrrolidone, propylene glycol and dimethyl sulfoxide may be used. Among them, propylene glycol is especially preferred. The amount is 0.5-20% by weight, preferably 1-10% by weight. When the amount is 0.5% by weight or less, it shows insufficient solubility of the drug in the preparation and consequently causes the adverse effects on physical properties of the preparation, such as decrease in transdermal absorption or crystallization of the drug in the preparation. Also, when the amount is 20% by weight or more, it has adverse effects on physical properties of the preparation, such as increased irritation to the skin and decreased cohesion of the base materials.

The amount of styrene•isoprene•styrene block copolymer used in the adhesive layer of the present invention is 5-50% by weight, preferably 10-30% by weight. When the amount is 5% by weight or less, the problem arises that an insufficient cohesion of the adhesive layer leads to remaining of the base materials on the skin, and when the amount is 50% by weight or more, it coheres too much to cause reduction of adhesion or decrease of efficiency in kneading process.

Usually, a tackifier resin is mixed with styrene•isoprene•styrene block copolymer to give adhesiveness to the skin, and the amount is 20-50% by weight, more preferably 20-35% by weight. When the amount of the tackifier resin is less than 20% by weight, the adhesion property of the external patch become worse, and when the amount is more than 50% by weight, it shows too much tackiness and causes physical skin-irritation by peeling off the patch from the skin. Examples of the tackifier resin used in the present invention are one or more resins selected from rosin resins, terpene resins, petroleum resins, phenol resins, xylene resins and the like, and especially hydrogenated rosin glycerol esters and alicyclic saturated hydrocarbon resins are preferred.

The adhesive layer of the present invention may further contain a softening agent such as fats and oils, for example liquid paraffin, vaseline and the like, liquid rubbers, for example, polybutene, polyisobutylene, polyisoprene and the like, and the amount is 5-70% by weight, more preferably 20-60% by weight. Especially, liquid paraffin and polybutene are preferred.

The present invention may further contain transdermal absorption enhancers for enhancing the transdermal absorbability of diclofenac hydroxyethylpyrrolidine. Specifically, the transdermal absorption enhancers may include, for example, fatty acid esters such as isopropyl myristate, diisopropyl adipate and the like, higher fatty acids such as isostearic acid, oleic acid, myristic acid and the like, amines such as diisopropanol amine, triethanol amine and the like, and surfactants such as sorbitan monooleate, lauromacrogol and the like.

The adhesive layer of the present invention may further contain an acidic polymer. When adding the acidic polymer to the oily patch of the present invention, a part or all of diclofenac hydroxyethylpyrrolidine salt is converted to a free acid form of diclofenac, and consequently the transdermal absorption of the drug is improved. As the acidic polymer used in the present invention, polyacrylic acid is especially preferred and its amount is 0.1-10% by weight, more preferably 0.1-5% by weight.

Furthermore, as the base materials used in the present invention, the materials conventionally used in the preparation for a patch are optionally selected and added suitably as appropriate in order to control adhesiveness and stability of the base materials. In particular, an appropriate amount of a water-absorbing polymer such as polyvinylpyrrolidone, polyvinylpyrrolidone/vinyl acetate copolymer and the like, an inorganic filler such as titanium dioxide, silicas and the like, an antioxidant such as dibutylhydroxytoluene and the like may be optionally contained.

The backing of the oily patch of the present invention is preferably a flexible and stretchable material including but not limited to a polyester woven fabric, a nonwoven fabric, a low-density polymer film and the like, and the material can be optionally selected.

The release liner used in the present invention includes such as polyethylene terephthalate, polypropylene, paper and the like. The release liner may be optionally siliconized as appropriate to adjust peel force optimally.

The oily patch of the present invention can be prepared by the following method for example. The drug solution is prepared by dissolving diclofenac hydroxyethylpyrrolidine in the above-mentioned solubilizers by warming. Separately, styrene•isoprene•styrene block copolymer, a softening agent (for example, polybutene, liquid paraffin and the like), a tackifier resin, and optionally, an antioxidant, an acidic polymer and the like are mixed under heating with stirring. To the adhesive base materials is added the drug solution, and the mixture is stirred until the solution becomes uniform. Thus formed adhesive layer is spread on a liner by a known method and laminated on a backing. Then, by cutting the patch into a suitable size and shape, the external patch of the present invention can be obtained. In this case, the suitable amount of the adhesive layer to be coated is 50-400 $g/m^2$, preferably 100-200 $g/m^2$.

EXAMPLES

Hereinafter, the present invention will be explained more specifically with Examples below, however the present invention is not intended to be limited to them by any means. The numerical values in the Examples are "% by weight" unless otherwise indicated.

Examples

According to the above-mentioned method with formulas in Table 1, the oily patch of each Example was prepared.

TABLE 1

| Composition/Example | Ex. 1 | Ex. 2 | Ex. 3 | Ex. 4 |
|---|---|---|---|---|
| Diclofenac hydroxyethylpyrrolidine | 5 | 5 | 5 | 5 |

TABLE 1-continued

| Composition/Example | Ex. 1 | Ex. 2 | Ex. 3 | Ex. 4 |
|---|---|---|---|---|
| N-Methyl-2-pyrrolidone | | 3 | | 3 |
| Propylene glycol | 5 | | | |
| Dimethyl sulfoxide | | | 3 | |
| Styrene · soprene · styrene block copolymer | 11 | 11 | 11 | 11 |
| Hydrogenated rosin glycerol ester | 25 | 30 | 25 | 30 |
| Alicyclic saturated hydrocarbon resin | | | 5 | |
| Polybutene | 10 | 10 | 5 | 10 |
| Liquid paraffin | 43.5 | 38.5 | 45.5 | 37 |
| Dibutylhydroxytoluene | 0.5 | 0.5 | 0.5 | 2 |
| Lauromacrogol | | 2 | | |
| Triethanolamine | | | | 1 |
| Polyacrylic acid | | | | 1 |
| Total | 100 | 100 | 100 | 100 |

Comparative Example

Using Example 1 of Patent document 2 as a reference, the external patch (cataplasm) of Comparative Example 1 with the formula in Table 2 was prepared.

TABLE 2

| Composition/Comparative Example | Comp. Ex. 1 |
|---|---|
| Diclofenac hydroxyethylpyrrolidine | 1.3 |
| Sodium polyacrylate | 4 |
| Sodium carboxymethyl cellulose | 3 |
| Gelatin | 2 |
| Polyvinylpyrrolidone | 2 |
| 1,3-Butanediol | 20 |
| D-Sorbitol solution | 20 |
| Kaolin | 5 |
| Titanium oxide | 0.5 |
| Aluminum hydroxide | 0.8 |
| Tartaric acid | 0.3 |
| Methylparaben | 0.1 |
| Propylparaben | 0.05 |
| Purified water | appropriate amount |
| Total | 100 |

Test Example 1

Rat Skin Permeability Test in vitro

To study transdermal absorbability of diclofenac hydroxyethylpyrrolidine in the oily patch of the present invention, rat skin permeability test in vitro was conducted on Examples 1-4 and Comparative Example 1. The excised abdominal skin of Wistar rats was put in a Franz diffusion cell, and each test preparation which was cut in round shape (φ14 mm) was applied to it. The receptor side was filled with phosphate buffered saline, and hot water of 37° C. was circulated in the water jacket. The solution of the receptor side was sampled at each time of the time course and the amount of diclofenac hydroxyethylpyrrolidine permeated the skin was measured by liquid chromatography.

The results are shown in FIG. 1.

Test Example 2

Primary Skin Irritation Test in Rabbit

Primary skin irritation test on Examples 1-4 and Comparative Example 1 by Draize method was conducted using rabbits. To intact and abraded back skin of the rabbits, each test preparation was applied for 24 hours and then removed. One, 24 and 48 hours after the removal of the preparation, the skin manifestation was visually evaluated according to the evaluation criteria of Table 3, and irritation score of each test preparation was calculated. The evaluation criteria for the irritation score are shown in Table 3-1 and the results of the measurements are shown in Table 3-2.

TABLE 3-1

Evaluation criteria

| Erythema and eschar formation | Value | Edema formation | Value |
|---|---|---|---|
| No erythema | 0 | No edema | 0 |
| Very mild erythema | 1 | Very mild edema | 1 |
| Well-defined erythema | 2 | Mild edema | 2 |
| Moderate to severe erythema | 3 | Moderate edema | 3 |
| Severe erythema to mild eschar formation | 4 | Severe edema | 4 |

Irritation score = [total value at one and 48 hours after removal]/4
Evaluation of irritation: irritation score = 0; non irritation,
0 < irritation score < 2; mild irritation, 2 ≤ irritation score < 5; moderate irritation,
5 ≤ irritation score; severe irritation

TABLE 3-2

| Test preparation | Ex. 1 | Ex. 2 | Ex. 3 | Ex. 4 | Comp. Ex. 1 |
|---|---|---|---|---|---|
| Irritation score | 1.2 | 1.2 | 1.3 | 1.0 | 1.2 |

Test Example 3

Stability Test

On Examples 1-4, the drug stability in the patch was evaluated. After storing each test preparation for 6 months at 40° C., the drug concentration of the collected sample was measured by liquid chromatography. The remaining drug ratio (% to the initial amount) of each preparation after storing was calculated using the amount of diclofenac hydroxyethylpyrrolidine in each preparation before the test as the initial amount (100%). The results are shown in Table 4.

TABLE 4

| Storage condition | Ex. 1 | Ex. 2 | Ex. 3 | Ex. 4 |
|---|---|---|---|---|
| Initial amount | 100.0 | 100.0 | 100.0 | 100.0 |
| 40° C.-6 months | 98.9 | 98.1 | 97.9 | 98.1 |

From the above results of each test, it was found that the oily patch of the present invention was as safe as the cataplasm of the Comparative Example and the patch showed much higher transdermal absorbability than the cataplasm. It was also found that the patch showed very excellent stability of the drug. That is to say, the oily external patch containing diclofenac hydroxyethylpyrrolidine of the present invention is an external patch with excellent transdermal absorbability, safety and stability of the drug.

The invention claimed is:

1. An oily external patch containing diclofenac hydroxyethylpyrrolidine prepared by laminating an adhesive layer on a backing, wherein said adhesive layer comprises 5-50% by weight of styrene•isoprene•styrene block copolymer, 20-50% by weight of a tackifier resin, 5-70% by weight of a softening agent, and 0.5-20% by weight of one or more solubilizers selected from N-methyl-2-pyrrolidone, propylene glycol and dimethyl sulfoxide as essential ingredients and 0.5-20% by weight of diclofenac hydroxyethylpyrrolidine as an active ingredient.

2. The external patch containing diclofenac hydroxyethylpyrrolidine according to claim 1 characterized in that said adhesive layer further contains an acidic polymer.

* * * * *